(12) United States Patent
Loenner et al.

(10) Patent No.: US 11,077,263 B2
(45) Date of Patent: Aug. 3, 2021

(54) DISPOSABLE AMPOULE FOR AN AEROSOL GENERATING DEVICE

(71) Applicant: PARI Pharma GmbH, Starnberg (DE)

(72) Inventors: Mihaela Loenner, Poing (DE); Thomas Gallem, Munich (DE); Uwe Hetzer, Munich (DE)

(73) Assignee: PARI Pharma GmbH, Starnberg (DE)

( * ) Notice: Subject to any disclaimer, the term of this patent is extended or adjusted under 35 U.S.C. 154(b) by 269 days.

(21) Appl. No.: 14/992,156

(22) Filed: Jan. 11, 2016

(65) Prior Publication Data

US 2016/0199597 A1 Jul. 14, 2016

Related U.S. Application Data

(63) Continuation of application No. 12/275,512, filed on Nov. 21, 2008, now Pat. No. 9,265,900.

(30) Foreign Application Priority Data

Nov. 23, 2007 (DE) .......................... 102007056462.9

(51) Int. Cl.
*A61M 11/00* (2006.01)
*A61J 1/06* (2006.01)
(Continued)

(52) U.S. Cl.
CPC .......... *A61M 15/0031* (2014.02); *A61J 1/067* (2013.01); *A61M 11/00* (2013.01); *A61M 11/005* (2013.01); *A61M 15/004* (2014.02); *A61M 15/009* (2013.01); *A61M 15/0028* (2013.01); *A61M 15/0036* (2014.02);
(Continued)

(58) Field of Classification Search
CPC ........ A61M 2005/2418; A61M 15/003; A61M 15/0031; A61M 15/0065; B05B 17/06
See application file for complete search history.

(56) References Cited

U.S. PATENT DOCUMENTS 2,431,649 A 11/1947 Moats
3,171,412 A 3/1965 Braun
(Continued)

FOREIGN PATENT DOCUMENTS

CA 2 619 605 A1 2/2007
CH 520530 A 3/1972
(Continued)

OTHER PUBLICATIONS

International Preliminary Report on Patentability dated Feb. 28, 2008 from International Application No. PCT/EP2006/008086.
(Continued)

*Primary Examiner* — Nathan R Price
*Assistant Examiner* — Weng Lee
(74) *Attorney, Agent, or Firm* — Wolf, Greenfield & Sacks, P.C.

(57) ABSTRACT

Disposable ampoule for use in an aerosol generating device, comprising: a medicament container that contains a medicament and is formed of a container body and a container bottom, and a predetermined break point that at least partly surrounds the container bottom, characterised by a collar that surrounds the predetermined break point at its outside and extends the container body over and beyond the container bottom.

15 Claims, 3 Drawing Sheets

Figure 3:
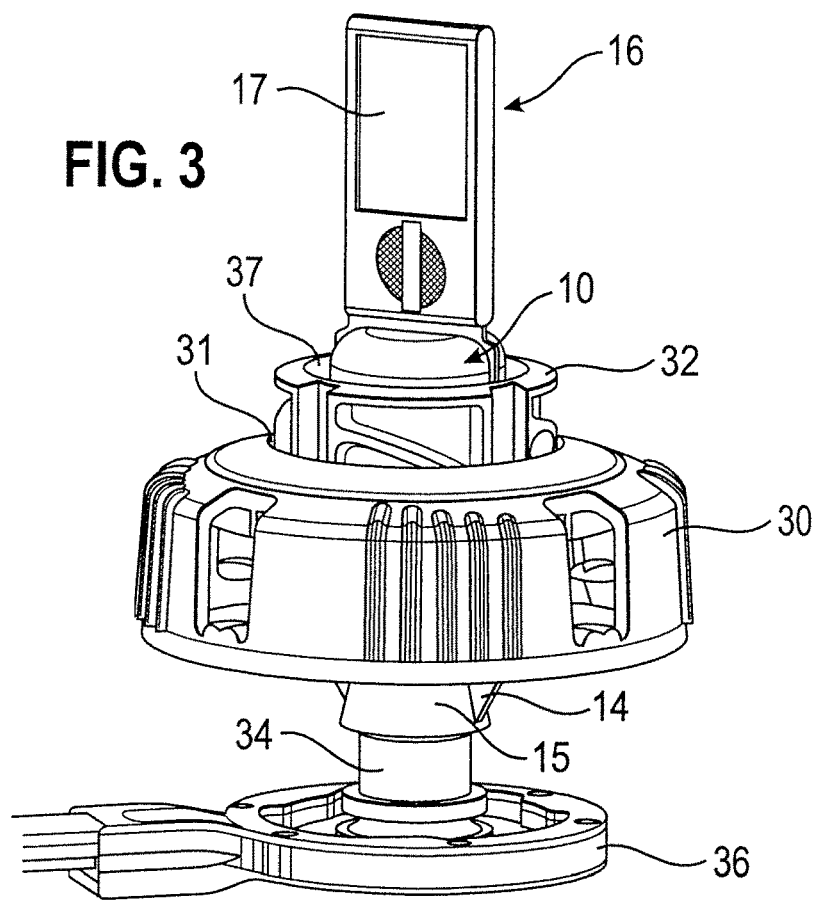
Figure 4:
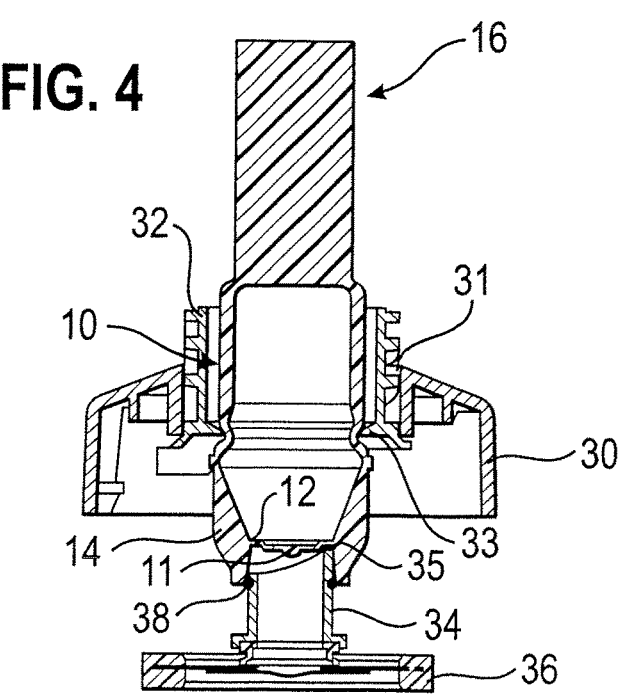

(51) Int. Cl.
*B65D 1/09* (2006.01)
*A61M 15/00* (2006.01)
*B65D 1/02* (2006.01)

(52) U.S. Cl.
CPC .......... *B65D 1/0238* (2013.01); *B65D 1/095* (2013.01); *A61M 15/0085* (2013.01); *A61M 2202/0468* (2013.01); *A61M 2205/6054* (2013.01); *A61M 2205/6072* (2013.01); *A61M 2207/00* (2013.01); *A61M 2210/0618* (2013.01); *A61M 2210/1039* (2013.01)

(56) References Cited

U.S. PATENT DOCUMENTS

| | | | |
|---|---|---|---|
| 3,237,809 A | 3/1966 | Daragan et al. | |
| 3,913,631 A | 10/1975 | Guichard et al. | |
| 3,919,374 A | 11/1975 | Komendowski | |
| 4,052,986 A * | 10/1977 | Scaife | A61M 31/00 604/204 |
| 4,133,312 A | 1/1979 | Burd | |
| 4,671,763 A * | 6/1987 | Weiler | B29C 49/42 264/524 |
| D312,209 S * | 11/1990 | Morrow | D9/443 |
| 4,995,511 A | 2/1991 | Evans | |
| 4,995,519 A * | 2/1991 | Rose | A61J 1/067 206/532 |
| 5,009,309 A | 4/1991 | Hansen | |
| 5,048,514 A | 9/1991 | Ramella | |
| 5,152,284 A | 10/1992 | Valentini et al. | |
| 5,337,740 A | 8/1994 | Armstrong et al. | |
| 5,364,386 A | 11/1994 | Fukuoka et al. | |
| 5,379,898 A * | 1/1995 | Joulia | A61J 1/065 206/528 |
| 5,399,159 A | 5/1995 | Chin et al. | |
| 5,435,282 A | 7/1995 | Haber et al. | |
| 5,515,842 A | 5/1996 | Ramseyer et al. | |
| 5,529,059 A | 6/1996 | Armstrong et al. | |
| 5,619,985 A | 4/1997 | Ohki et al. | |
| 5,647,349 A | 7/1997 | Ohki et al. | |
| 5,715,810 A | 2/1998 | Armstrong et al. | |
| 5,921,236 A | 7/1999 | Ohki et al. | |
| 5,950,619 A | 9/1999 | van der Linden et al. | |
| 5,970,974 A | 10/1999 | van der Linden et al. | |
| 6,059,749 A | 5/2000 | Marx | |
| 6,145,703 A | 11/2000 | Opperman | |
| 6,197,260 B1 | 3/2001 | Bradshaw et al. | |
| 6,367,473 B1 | 4/2002 | Käfer | |
| 6,443,152 B1 | 9/2002 | Lockhart et al. | |
| 6,481,435 B2 | 11/2002 | Hochrainer et al. | |
| 6,510,847 B1 * | 1/2003 | Helgesson | A61M 15/0065 128/200.23 |
| 6,668,827 B2 | 12/2003 | Schuler et al. | |
| 6,708,846 B1 | 3/2004 | Fuchs et al. | |
| 6,832,703 B1 * | 12/2004 | Scott | B67B 7/92 222/1 |
| 6,851,626 B2 | 2/2005 | Patel et al. | |
| 6,877,672 B2 | 4/2005 | Stihl | |
| 6,948,491 B2 * | 9/2005 | Loeffler | A61M 15/0028 128/200.14 |
| 6,948,494 B1 | 9/2005 | Snow | |
| 6,971,385 B1 | 12/2005 | Flora | |
| 7,032,590 B2 * | 4/2006 | Loeffler | A61J 1/065 128/200.24 |
| 7,040,316 B2 | 5/2006 | Connelly et al. | |
| 7,100,600 B2 | 9/2006 | Loeffler et al. | |
| 7,185,790 B2 | 3/2007 | Weiler | |
| 7,261,102 B2 | 8/2007 | Barney et al. | |
| 7,270,127 B2 | 9/2007 | Lockhart et al. | |
| 7,360,536 B2 | 4/2008 | Patel et al. | |
| 7,681,572 B2 | 3/2010 | Fishman | |
| 8,047,394 B2 | 11/2011 | Hansen | |
| 8,074,642 B2 | 12/2011 | Bruce | |
| 9,265,900 B2 | 2/2016 | Loenner et al. | |
| 9,789,270 B2 | 10/2017 | Hetzer et al. | |
| 2002/0092521 A1 * | 7/2002 | Sullivan | A61M 15/0028 128/200.24 |
| 2002/0129812 A1 | 9/2002 | Litherland et al. | |
| 2002/0134372 A1 | 9/2002 | Loeffler et al. | |
| 2003/0140921 A1 | 7/2003 | Smith et al. | |
| 2004/0010242 A1 | 1/2004 | Heyes et al. | |
| 2004/0126325 A1 * | 7/2004 | Lewis | B65D 83/38 424/45 |
| 2004/0134494 A1 | 7/2004 | Papania et al. | |
| 2004/0256487 A1 | 12/2004 | Collins et al. | |
| 2005/0051166 A1 | 3/2005 | Glusker et al. | |
| 2005/0056281 A1 | 3/2005 | Snow | |
| 2005/0150492 A1 | 7/2005 | Dunkley et al. | |
| 2005/0161041 A1 | 7/2005 | Schuler et al. | |
| 2005/0263618 A1 | 12/2005 | Spallek et al. | |
| 2006/0027233 A1 | 2/2006 | Zierenberg et al. | |
| 2006/0054165 A1 | 3/2006 | Hughes et al. | |
| 2006/0057257 A1 | 3/2006 | Ma | |
| 2006/0150969 A1 | 7/2006 | Connelly et al. | |
| 2007/0107720 A1 | 5/2007 | Boeck et al. | |
| 2007/0163574 A1 | 7/2007 | Rohrschneider et al. | |
| 2007/0240706 A1 | 10/2007 | Kobayashi et al. | |
| 2008/0123465 A1 * | 5/2008 | Heusser | B01F 5/064 366/130 |
| 2009/0137950 A1 | 5/2009 | Loenner et al. | |
| 2009/0223513 A1 | 9/2009 | Papania et al. | |
| 2009/0293868 A1 * | 12/2009 | Hetzer | A61M 15/0085 128/200.14 |
| 2018/0064891 A1 | 3/2018 | Hetzer et al. | |

FOREIGN PATENT DOCUMENTS

| | | |
|---|---|---|
| DE | 38 23 428 A1 | 1/1990 |
| DE | 38 33 036 A1 | 4/1990 |
| DE | 43 06 458 A1 | 9/1994 |
| DE | 102 53 237 A1 | 5/2004 |
| DE | 10 2005 038 619 A1 | 2/2007 |
| EP | 0 326 391 A2 | 8/1989 |
| EP | 1 186 350 A1 | 3/2002 |
| JP | 50-64490 U | 10/1973 |
| JP | 3094233 U | 9/1991 |
| JP | 10-151199 | 6/1998 |
| JP | 10-179739 | 7/1998 |
| JP | 2003-521977 A | 7/2003 |
| WO | WO 00/66277 A1 | 11/2000 |
| WO | WO 01/58236 A2 | 8/2001 |
| WO | WO 02/074372 A2 | 9/2002 |
| WO | WO 02/074373 A1 | 9/2002 |
| WO | WO 02/074374 A1 | 9/2002 |
| WO | WO 2005/028006 A1 | 3/2005 |
| WO | WO 2006/006963 A2 | 1/2006 |
| WO | WO 2006/032320 A1 | 3/2006 |
| WO | WO 2007/020073 A1 | 2/2007 |

OTHER PUBLICATIONS

Search Report dated May 7, 2009 from European Application No. 0816901.
English Translation of Examination Report dated Mar. 19, 2013 from Japanese Application No. 2010-286147.
Indian Examination Report dated Sep. 22, 2017 in connection with Indian Application No. 2027/KOL/2008.
Indian Summons to Attend Hearing dated Jan. 28, 2020 in connection with Indian Application No. 2027/KOL/2008.

* cited by examiner

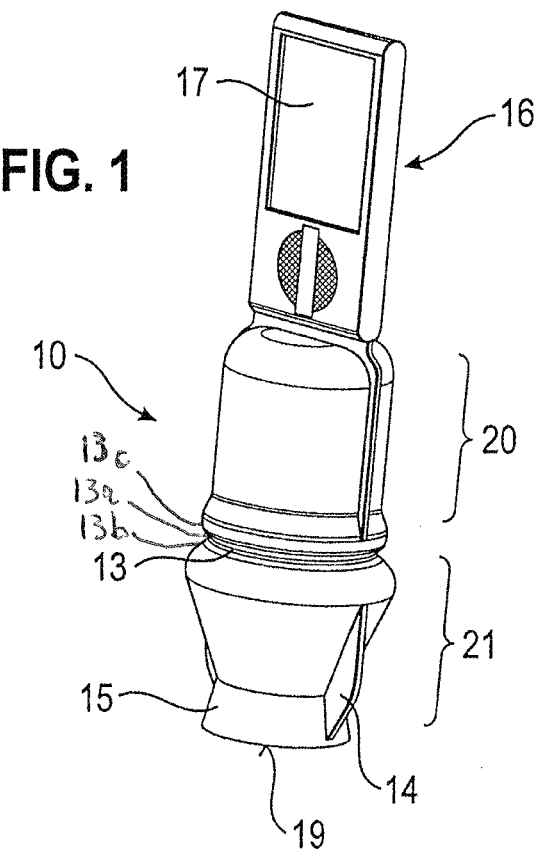
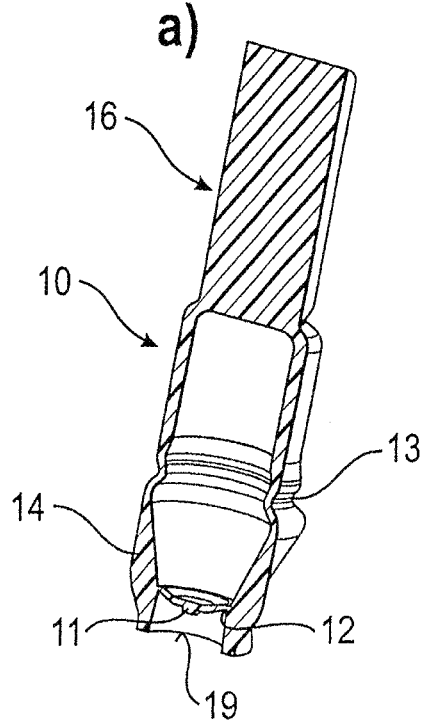
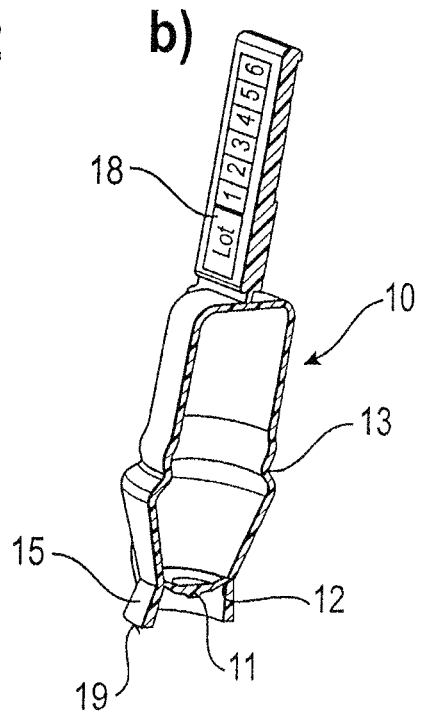
FIG. 1
FIG. 2

DISPOSABLE AMPOULE FOR AN AEROSOL GENERATING DEVICE

CROSS REFERENCE TO RELATED APPLICATIONS

This application is a continuation of U.S. application Ser. No. 12/275,512 filed Nov. 21, 2008, which claims the priority benefit of German Application. No. 10 2007 056 462.9 filed Nov. 23, 2007, which are hereby incorporated by reference to the maximum extent allowable by law.

The present invention relates to a disposable ampoule for use in a device that can be used to generate aerosols for topical application to the skin or body cavities such as, for example, the nose and lungs in order to diagnose, prevent or treat illnesses in humans and animals. It substantially relates to a disposable ampoule that is filled with a liquid medicament and is first opened in the device so as to supply the liquid medicament to an aerosol generator that can be designed such that an aerosol is generated and released in a continuous, timed or respiration-controlled manner so as to diagnose, prevent or treat illnesses therewith.

Such a disposable cartridge is known from DE 10 2005 038 619 A1. The disposable ampoule described therein comprises a medicament container that contains a medicament and is composed of a container body and a container bottom as well as a predetermined break point surrounding the container bottom. By means of a needle that is generally provided in the aerosol generating device, the bottom of the container is pierced along the predetermined break point in order to open the disposable ampoule and to supply the liquid medicament to the aerosol generator.

The object of the present invention is now to further develop this known disposable ampoule such that it can be handled and inserted in the aerosol generating device easily and without the risk of damage, such that no medicament can escape during the opening process of the ampoule when it is inserted and such that also when the aerosol is being generated, the interface between the aerosol generating device and the ampoule is sealed so that contamination or an unintentional escape of the medicament is prevented.

This object is solved according to the present invention by means of a disposable ampoule having the features of patent claim 1. Advantageous further developments of the present invention are mentioned in the dependent patent claims.

The idea forming the basis for the present invention is to encircle the bottom of the container as well as the predetermined break point that at least partly surrounds the container bottom with a protective collar so that an unintentional opening or breaking open of the ampoule outside of the aerosol generating device owing to damage to the predetermined break point can be prevented. In addition to this function, it has also been proven in an advantageous manner that the collar can be used for sealing during and optionally also after the opening process as well as for guiding the ampoule during this process.

Accordingly, the disposable ampoule for use in an aerosol generating device according to the present invention comprises a medicament container that contains a medicament, in particular a liquid medicament, and is formed of a container body and a container bottom as well as a predetermined breaking point that at least partly surrounds the bottom of the container. The disposable ampoule according to the invention is characterised by a collar that surrounds the predetermined break point at its outside and extends the container body over and beyond the bottom of the container. The bottom of the container and the predetermined breaking point that surrounds it are thus rearwardly displaced at a distance to the front end of the disposable ampoule and are therefore protected by the collar. In addition to protection, this displacement has the further advantage that during the opening process of the disposable ampoule in the aerosol generating device, for example on a needle, an inner surface of the collar can be engaged with a sealing element, for example an o-ring or a sealing edge surrounding the needle, when the disposable ampoule is not yet opened such that sealing is also ensured during the opening process. Furthermore, owing to its design, the collar also has a guiding function and thus facilitates a neat positioning of the ampoule during the opening process.

The inner surface of the collar advantageously expands in a conical manner starting from the bottom of the container. The entire collar can be designed in the form of a hollow truncated cone for this purpose. This design advantageously supports the guiding function of the collar and the engagement with a possible additional sealing element on the piercing member (needle) of the aerosol generating device.

It is furthermore preferred to divide the container body into two functional areas so that the ampoule has a modular construction. It has proven to be particularly advantageous here for a first functional area comprising the container bottom to be geometrically designed with respect to the no-load behaviour of the ampoule and for it to stay the same at least in the case of all ampoules intended for the same aerosol generating device, regardless of the size and filling amount, whereas the second functional area, on the other hand, is configured in a substantially cylindrical manner and, so as to adapt to different filling amounts, is accordingly designed with different lengths. This in particular enables the use of the same aerosol generating device with substantially the same ampoules that differ solely as regards their length, which is advantageous for both reasons of production technology and from the point of view of user-friendliness. The first functional area of the ampoule, which faces the aerosol generating device and thus comprises the container bottom, is thereby designed such that the medicament can be supplied to the aerosol generator with a reproducible dosage accuracy, whereby inter alia the different holding angles of the aerosol generating device during therapy are to be taken into consideration. It has thereby proven to be advantageous if, at least inside the ampoule, this first functional area extends in a conical manner, i.e. in a funnel shape, in the direction of the container bottom, with the angle between the bottom of the container and the funnel-shaped side wall preferably being in the range of approximately 105° to 125° and preferably being 110°. Furthermore, the ampoule and in particular this first functional area can be designed in various manners also in the case of ampoules that are intended for different aerosol generating devices, namely such that in each case only the ampoule intended for the respective aerosol generating device can be inserted in such a device and/or the aerosol generating device is only capable of functioning with a predetermined ampoule. This type of identification or coding can be realised, for example, by means of one or more coding elements. These can consist, for example, of one or more projections that extend from the ampoule body. These projections, which fit into corresponding grooves in the aerosol generating device intended therefor, allow insertion of the ampoule or prevent insertion if the combination is not correct. The one or more projections can also be used to activate an electric switch in order to close a circuit in the aerosol generating device. Only when the circuit is closed could, for example, power be supplied to the aerosol generator or aerosol producer. Alternatively, the coding elements can be designed such that they prevent operation of the aerosol generating device unless they are correctly recognised by the aerosol generating device. For example, the container body can comprise a readable pattern such as, for instance, a barcode, a magnetic pattern or the like, which must be read out and confirmed by the aerosol generating device before operation is permitted.

So that the ampoule can be securely inserted in the aerosol generating device and the empty ampoule can be easily removed again, a fixing groove that preferably extends in a circular manner around the ampoule is provided centrally or closer to the bottom of the container in the longitudinal direction of the ampoule. Its position in the centre of the ampoule or closer to the container bottom thereby has the advantage that the forces required to open the ampoule, which arise when breaking the predetermined break point by means of the piercing member (needle), can be absorbed as close as possible to the region where the force is introduced. If the ampoule, as described above, is divided into two functional areas, it has proven to be advantageous if the fixing groove divides the ampoule into the two functional areas.

In order to additionally strengthen the ampoule and to counteract deformation during the opening process, at least one reinforcing rib is provided on the container body. Preferably two diametrically opposed reinforcing ribs are provided. It is preferred for these ribs to extend from the front end of the ampoule, i.e. over at least a partial area of the collar, over and beyond the bottom of the container and over a partial area of the container body. If the ampoule is divided into two functional areas, it is thereby particularly preferred for the reinforcing ribs to be provided only in the first functional area or if a fixing groove is provided, on the side of the fixing groove comprising the bottom of the container.

It is furthermore necessary to visibly label the ampoule such that medicament, batch number and expiry date are apparent. This is solved according to the invention in that opposite the container bottom, a lug is provided on the container body, which preferably extends away from the container body in the opposite direction to the collar. This lug comprises two opposite planar sides, on which the necessary information can be provided. This lug can be additionally used to facilitate the removal of the ampoule, i.e. it can form a grip tab which the user can grip to push or pull the ampoule out of the aerosol generating device. This is particularly useful in the case of short ampoules for small filling amounts (see modular construction). For this purpose, the aerosol generating device is preferably designed such that the lug for removing the ampoule is exposed. It is thereby also particularly preferred for the lug to protrude out of the aerosol generating device when the ampoule is inserted in the aerosol generating device such that the aforementioned information remains visible in this case as well.

According to one embodiment of the present invention, the ampoule is formed in an integral manner and is preferably a blow-fill-seal ampoule, which means that the ampoule is produced by the so-called blow-fill-seal process. This technique is known, for example, from DE 38 33 036, DE 38 23 428 and U.S. Pat. Nos. 4,671,763, 3,919,374 and 4,995,511, and thus the person skilled in the art is referred to these documents as regards the technique as such. The ampoule is preferably made of polyethylene, polypropylene or a thermoplastic copolymer.

Finally, the integral or also multi-piece ampoule may have or can be provided with an additional element, with this additional element being a separate sealing element that is inserted in the collar in order to bring about a seal between the inner surface of the collar and the piercing member (for example a needle) when inserting the ampoule into the aerosol generating device and in particular during the opening process.

In order to avoid the formation of air bubbles during the outflow of the medicament, it is furthermore preferred that the opening diameter of the ampoule, which consists of the diameter of the container bottom and the diameter and at least a part of the predetermined break point, is greater than approximately 8 mm and is preferably in a range of between approximately 8 mm and approximately 15 mm. According to a particularly preferred embodiment, the opening diameter is approximately 10 mm. It is accordingly preferred for the piercing member of the aerosol generating device, for example a needle, to have an internal diameter of at least approximately 8 mm.

The medicament container of the ampoule described above preferably contains up to 10 ml, most preferably between 0.25 and 5 ml of medicament. Within this volume range, it is possible by way of the dimensioning and design in particular of the second functional area, as explained above, to precisely dose volumes with an accuracy of ±25% to ±5% of the target volume.

According to a preferred embodiment, the medicament contained in the ampoule comprises at least one active agent and preferably at least one auxiliary agent in dissolved or suspended form. The medicament is preferably a medicament for the diagnosis, prophylaxis or treatment of illnesses in humans and animals in nebulised form, with it being possible, in combination with a perforated oscillating membrane, to nebulise the medicament into droplets having a mean diameter of <6 μm or to nebulise it as a pulsating aerosol having such a mean mass diameter. As regards the medicaments and the additives and auxiliary agents that can possibly be used, reference is made to the following description.

Accordingly, the present invention furthermore relates to the use of an ampoule according to the invention in an aerosol generator, with the medicament thereof being nebulised by an aerosol generator and used for local, nasal or pulmonary application.

Further advantages and features of the present invention become apparent from the following description of a preferred embodiment, which takes place with reference to the accompanying drawings.

FIG. 1 shows a perspective view of a disposable ampoule according to the invention;

FIGS. 2A and 2B each show a cross-section through the ampoule according to the invention, with FIG. 2A showing a cross-section parallel to and through the reinforcing ribs as well as the lug, and FIG. 2B showing a cross-section perpendicular to the cross-section of FIG. 2A;

FIG. 3 shows a perspective view of a part of an aerosol generating device with an inserted ampoule;

FIG. 4 shows a cross-section through the arrangement shown in FIG. 3;

FIG. 5 shows an enlargement of the interface between the ampoule and needle of FIG. 4; and FIG. 6 shows the interface shown in FIG. 5 with an opened container bottom, i.e. with an inserted ampoule.

FIG. 1 shows a disposable ampoule according to the invention which comprises a medicament container that contains a liquid medicament (not shown) and consists of a container body 10 and a container bottom 11 (see FIGS. 2A and 2B). The container body 10 is substantially constructed as a hollow cylinder and the container bottom 11 has a substantially circular design with a diameter (including a predetermined break point 12) of greater than approximately 8 mm in order to prevent the formation of air bubbles that could impede the subsequent flow of the medicament. The diameter is preferably about 10 mm. The predetermined break point 12 is formed between the container bottom 11 and the container body 10. The predetermined break point 12 at least partly surrounds the bottom 11 of the container, however, it preferably and as shown completely surrounds the container bottom and has an annular shape. The predetermined break point 12 is brought about, for example, by a weakness in the material, i.e. the material strength of the predetermined break point 12 is reduced as compared to the material strength of the bottom 11 of the container.

As is shown in FIGS. 1, 2A and 2B, the ampoule according to the invention furthermore comprises a collar 15 that is also designed with an annular cross-section and which extends the container body 10 over and beyond the container bottom 12. The bottom of the container is therefore at a distance to the front end 19 and the predetermined break point 12 surrounding it is also protected by the collar 15 against damage and possible opening before use.

Starting from the container bottom, the collar 15 is thereby designed such that the cross-section of its inner contour becomes bigger, i.e. it is configured in a conical manner, with it expanding starting from the container bottom 11 (the diameter of the annular cross-section becomes bigger starting from the container bottom 11).

As is indicated in FIG. 1, the container body 10 comprises an annular surrounding fixing groove 13 that is slightly closer to the container bottom 11 in the longitudinal direction, said groove serving to mount (hold or fix) the ampoule in an aerosol generating device (see below). As shown in FIG. 1, the fixing groove 13 includes an annular indentation 13a into the container body 10 and first and second portions 13b and 13c of the container body 10 located on opposite sides of the annular indentation 13a, the first and second portions 13b and 13c being raised with respect to a bottom part of the annular indentation 13a and defining the annular indentation 13a between them. This fixing groove divides the container body into a first and second functional area. In addition to the collar 15, the first functional area 21 comprises a section of the container body 10, the geometric form of which is designed such that the medicament (not shown) contained in the ampoule can be supplied to the aerosol generating device and in particular the aerosol generator thereof with a reproducible dosage accuracy. For this purpose, the first functional area 21 extends in a conical manner towards the bottom of the container, i.e. its inner contour is formed in a funnel-shape in the direction of the container bottom 11. The second functional area 20 is substantially designed as a hollow cylinder. This design enables a modular construction of the ampoule according to the invention. The functional area 21 is therefore preferably the same in all ampoules regardless of the filling amount so that the interface between the ampoule and the aerosol generating device can remain unchanged, i.e. different ampoules can be inserted in the same aerosol generating device. Furthermore, the ampoules can also be designed such that they are only suitable for specific aerosol generating devices. Ampoules for an aerosol generating device can, for example, be designed such that they do not fit into another aerosol generating device and vice versa. So-called coding elements or identification elements can be provided for this purpose, which can include, for example, projections or barcodes or magnetic information. The projections can, for example, prevent insertion of the ampoule into the aerosol generating device if it is not intended for the corresponding aerosol generating device. On the other hand, the projections can also come into contact with an electric switch when the ampoule is inserted into the correct aerosol generating device in order to ensure operation of the aerosol generating device. The reading out of the information of the barcode or the magnetic information that enables operation of the aerosol generating device in the case of a correct ampoule also works in a similar manner. These elements are preferably also arranged in the first functional area. The second functional area 20, on the other hand, can vary in terms of its size in the longitudinal direction. In other words, the functional area 20 can be designed so as to be longer, i.e. have a larger volume, or shorter, i.e. have a smaller volume, depending on the filling amount of the respective ampoule. This is expedient both for manufacturing reasons for the production of various ampoules and also as regards user-friendliness since the user will always insert the ampoules into the aerosol generating device in the same manner regardless of their size. The operation thereof also remains the same. Finally, this design enables the use of various types of ampoules, i.e. with different filling amounts, in one and the same aerosol generating device.

The ampoule according to the invention furthermore comprises two diametrically opposed reinforcing ribs in the first functional area 21. These provide dimensional stability to the ampoule in particular during the opening process in which the ampoule is pushed onto a needle (see below) in order to pierce the bottom 11 of the container along the predetermined break point 12. In the embodiment shown in FIG. 1, the reinforcing ribs 14 extend over a portion of the collar 15 and over a portion of the section of the container body 10 that tapers into a funnel-shape.

A lug 16 is furthermore provided at the end of the container body 10 that is opposite the bottom 11 of the container. This lug, which has a substantially flat design with two opposite surface areas, enables the attachment of a labelling field 17, which can contain information about the accommodated medicament. The batch number 18 and the date of expiry can be provided on the opposite surface.

As is apparent from FIGS. 1, 2A and 2B, the ampoule according to the invention is formed in an integral manner. This advantageously occurs in the blow-fill-seal process. As regards this process, the person skilled in the art is referred to the aforementioned prior art publications. The ampoule can be made from polyethylene, polypropylene or a copolymer. The content has a variable yet previously definable volume range of approximately 0.25 ml to 5 ml and is supplied to an aerosol generator so that a medicament can be nebulised and used for topical application to the skin or body cavities, such as, for example, the nose and lungs, in order to diagnose, prevent or treat illnesses in humans and animals.

FIG. 3 shows part of an aerosol generating device. It comprises at least one lid 30, which is designed so as to be removable from the body of the aerosol generating device, for example so that it can be unscrewed. A through-hole 31 is provided in this lid, in which a first element 32 of the opening mechanism is inserted. Projections, for example, are provided on the inner circumference of the hole 31 of the lid 30, which engage in thread grooves in the element 32, or vice versa. By way of a rotational movement of the lid 30 when attaching the lid 30 to the body (not shown) of the aerosol generating device, the engagement of the projections of the lid 30 with the thread grooves of the element 32 causes a translational movement of the element 32. As regards this design, reference is made in particular to DE 10 2005 038 619 A1.

The element 32 furthermore comprises catches 33, with which the fixing groove 13 of the ampoule according to the invention can engage in order to fix the ampoule in the element 32.

The aerosol generating device furthermore comprises a needle 34 that is formed as a hollow cylinder and comprises a cutting edge 35 at its one end. The inner diameter of the needle 34 is greater than 8 mm in order to counteract the formation of air bubbles during the outflow of the medicament, which could impede the subsequent flow of the medicament. The aerosol generator, which is preferably a piezoelectrically actuated membrane, is located at the opposite end of the needle 34. A through-hole 37 is preferably also formed in the element 32 concentric to the hole 31 of the lid 30, through which the ampoule protrudes out of the aerosol generating device in the inserted state.

A further sealing element in the form of an o-ring 38 is additionally provided in the upper region of the needle 34.

The use of an ampoule according to the invention is explained in the following with reference to FIGS. 3 to 6.

Figure 5:
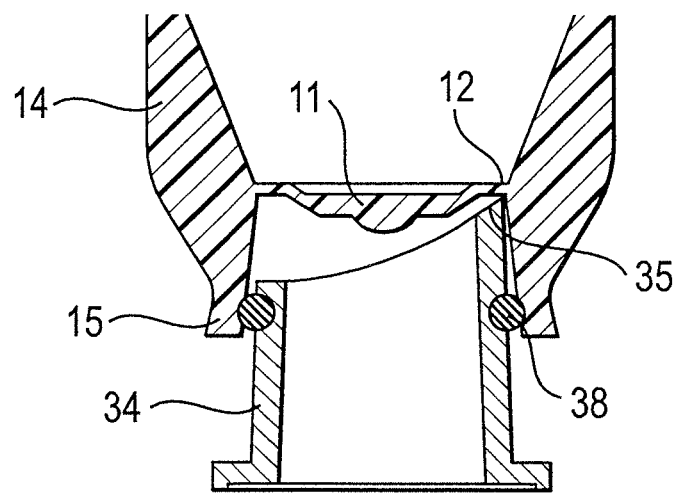

If an ampoule is to be inserted in the aerosol generating device, the lid 30 is removed from the body of the aerosol generating device, for example is unscrewed. The element 32 thereby moves upwards in a translational manner through the hole 31 of the lid 30. Once the lid has been removed, the ampoule is inserted into the element 32 from the side opposite the hole 37 of the element 32, with the lug 16 and part of the container body 10 being guided through the hole 37 of the element 32. The fixing projections 33 of the element 32 thereby engage with the fixing groove 13 of the ampoule and retain it in their longitudinal direction. The lid 30 is then placed back onto the body of the aerosol generating device. Owing to the twisting of the lid 30 and the engagement of the projections of the lid 30 with the thread grooves of the element 32, the element 32 is moved in a translational manner in the hole 31 of the lid 30. Since the ampoule is connected to the element 32, the ampoule is also moved in a translational manner. An inner surface of the collar 15 thereby first of all engages, as is shown in FIG. 5, with the o-ring 38 that completely surrounds the needle 34, and creates a reliable seal between the inner surface of the collar 15 and the outer surface of the needle 34. As is shown in FIG. 5, this occurs before the cutting edge 35 of the needle 34 starts the opening process, i.e. starts to cut through the predetermined break point 12. The ampoule is furthermore centred on the needle 34 by the conical inner contour of the collar 15. Owing to this design, medicament is reliably prevented from escaping during the opening process.

Furthermore, this seal is also maintained in the completely inserted state (FIG. 6), with it then being possible for there to be an optional seal also between the outer surface of the needle 34 and the inner surface of the container body directly at or above the bottom 11 of the container. A reliable insertion of the ampoule is furthermore ensured.

Figure 6:
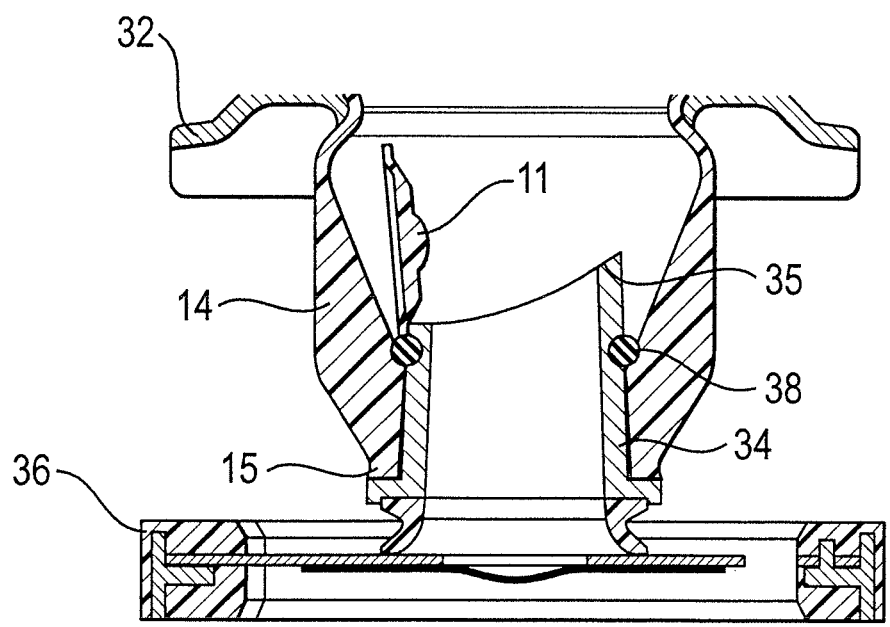

As a result of a further rotational movement of the lid 30 and the associated further translational movement of the element 32, and thus of the ampoule, the container bottom, as shown in FIG. 6, is pierced by the needle 34 and folded to one side so that the medicament contained in the ampoule can flow through the needle 34 to the aerosol generator 36. The funnel-shaped inner contour of the first functional region 20 of the container body 10 thereby brings about a supply of the medicament to the aerosol generator with a reproducible dosage accuracy. The arrangement of the fixing groove 13 in the centre or closer to the container bottom 12 in the longitudinal direction of the ampoule furthermore results in the forces required for opening the ampoule, which are transferred to the element 32 and thus the ampoule owing to the twisting of the lid, being absorbed as close as possible to the region where the force is introduced to the predetermined break point 12. Furthermore, the reinforcing ribs 14 strengthen the ampoule such that a deformation during the opening process is substantially prevented.

In the completely inserted state, the holes 37 of the element 31, 32 of the lid 30 are arranged substantially in one plane. However, the lug 16 protrudes through the hole 37 of the element 32 and out of the aerosol generating device in this position as well such that the labelling field 17 as well as the batch number 18 and the not shown expiry details are also still visible in the inserted state.

In order to remove the ampoule, the lid 30 is turned in the opposite direction, as a result of which the element 32 is moved in a translational manner in the opposite direction to when opening the ampoule, and the ampoule pulls away from the needle 34 again. The seal between the ampoule (collar) and the needle (o-ring) thereby remains until the ampoule can actually be removed from the needle 34 with the lid 30 and thus contamination of the device by medicament residues can also be prevented in this manner. In order to remove the ampoule from the lid 30, the user can grip the lug 16 and push the ampoule (downwards in the figures) out of engagement with the projections 33 such that it can be removed. The user must thereby not touch the area of the ampoule that is possible wetted by a medicament, which is additionally covered by the collar 15. Pushing out of the ampoule can also be facilitated in the case of a particularly short second functional area 20 owing to the at least protruding lug 16.

In summary, the present invention thus offers a plurality of advantages as compared to the ampoule of the prior art. It is, however, obvious that the described embodiment is only one possibility for carrying out the present invention and that the invention is defined by the following patent claims.

The active agent classes and/or substances listed in the following can be contained in the ampoule according to the invention, however this list is not conclusive:

The active compounds include, for example, substances selected from the group consisting of anti-inflammatory compounds, glucocorticoids, anti-allergy medicaments, antioxidants, vitamins, leukotrine antagonists, anti-infective agents, antibiotics, anti-fungicides, antiviral agents, mucolytic agents, decongestants, antiseptics, cyto-static agents, immunomodulators, vaccines, wound-healing agents, local anaesthetics, oligonucleotides, peptides, proteins and plant extracts.

Examples of potentially useful anti-inflammatory compounds are glucocorticoids and non-steroidal anti-inflammatory agents such as, for example, betamethasone, beclomethasone, budesonide, ciclesonide, dexamethasone, desoxymethasone, fluoconolone acetonide, flucinonide, flunisolide, fluticasone, icomethasone, rofleponide, triamcinolone acetonide, fluocortinbutyl, hydrocortisone, hydroxycortisone-17-butyrate, prednicarbate, 6-methylprednisolone aceponate, mometasone furoate, dehydroepiandrosterone sulphate (DHEAS), elastane, prostaglandin, leukotriene, bradykinin antagonists, non-steroidal anti-inflammatory medicaments (NSAIDs), such as ibuprofen, including any pharmaceutically acceptable salts, esters, isomers, stereoisomers, diastereomers, epimers, solvates or other hydrates thereof, prodrugs, derivates or any other chemical or physical forms of active compounds comprising the respective active residues.

Examples of anti-infective agents whose class or therapeutic category is understood herein as including compounds that are effective against bacterial, fungal and viral infections, i.e. including the classes of microbicides, antibiotics, fungicides, antiseptics and anti-viral agents, are

- penicillins, including benzylpenicillins (penicillin-G-sodium, clemizone penicillin, benzathine penicillin G), phenoxypenicillins (penicillin V, propicillin), aminobenzylpenicillins (ampicillin, amoxicillin, bacampicillin), acylaminopenicillins (azlocillin, mezlocillin, piperacillin, apalcillin), carboxypenicillins (carbenicillin, ticarcillin, temocillin), isoxazolylpenicillins (oxacillin, cloxacillin, dicloxacillin, flucloxacillin), and amiidine penicillins (mecillinam);
- cephalosporins, including cefazolins (cefazolin, cefazedone); cefuroximes (cerufoxime, cefamdole, cefotiam); cefoxitins (cefoxitin, cefotetan, latamoxef, flomoxef); cefotaximes (cefotaxime, ceftriaxone, ceftizoxime, cefmenoxime); ceftazidimes (ceftadzidime, cefpirome, cefepime); cefalexins (cefalexin, cefaclor, cefadroxil, cefradine, loracarbef, cefprozil), and cefiximes (cefixime, cefpodoxime proxetil, cefuroxime axetil, cefetamet pivoxil, cefotiam hexetil), loracarbef, cefepime, clavulanic acid/amoxicillin, ceftobiprole;
- synergists, including beta-lactamase inhibitors, such as clavulanic acid, sulbactam and tazobactam;
- carbapenems, including imipenem, cilastin, meropenem, doripenem, tebipenem, ertapenem, ritipenam and biapenem;
- monobactams, including aztreonam;
- aminoglycosides such as apramycin, gentamicin, amikacin, isepamicin, arbekacin, tobramycin, netilmicin, spectinomycin, streptomycin, capreomycin, neomycin, paromoycin and kanamycin;
- macrolides, including erythromycin, clarithromycin, roxithromycin, azithromycin, dithromycin, josamycin, spiramycin and telithromycin;
- gyrase inhibitors or fluroquinolones, including ciprofloxacin, gatifloxacin, norfloxacin, ofloxacin, levofloxacin, perfloxacin, lomefloxacin, garenoxacin, clinafloxacin, sitafloxacin, prulifloxacin, olamufloxacin, caderofloxacin, gemifloxacin, balofloxacin, trovafloxacin and moxifloxacin;
- tetracyclines, including tetracycline, oxytetracycline, rolitetracycline, minocycline, doxycycline, tigecycline and aminocycline;
- glycopeptides, including vancomycin, teicoplanin, ristocetin, avoparcin, oritavancin, ramoplanin and Peptide 4;
- polypeptides, including plectasin, dalbavancin, daptomycin, oritavancin, ramoplanin, dalbavancin, telavancin, bacitracin, tyrothricin, neomycin, kanamycin, mupirocin, paromomycin, polymyxin B and colistin;
- sulfonamides, including sulfadiazine, sulfamethoxazole, sulfalene, co-trimoxazole, co-trimetrol, co-trimoxazine, co-tetraxazine;
- azoles, including clotrimazole, oxiconazole, miconazole, ketoconazole, itraconazole, fluconazole, metronidazole, tinidazole, bifonazole, ravuconazole, posaconazole, voriconazole and ornidazole and other anti-fungicides including flucytosine, griseofluvine, tonoftal, naftifine, terbinafine, amorolfine, ciclopiroxolamine, echinocandin, such as micafungin, caspofungin, anidulafungin;
- nitrofuranes, including nitrofurantoin and nitrofuranzone;
- polyenes, including amphotericin B, natamycin, nystatin, flucocytosine;
- other antibiotics, including tithromycin, lincomycin, clindamycin, oxazolidinones (linezolids), ranbezolid, streptogramin A+B, pristinamycin aA+B, virginiamycin A+B, dalfopristin/quinupristin (synercid), chloramphenicol, ethambutol, pyrazinamide, terizidone, dapsone, prothionamide, fosfomycin, fucidin acid, rifampicin, isoniazid, cycloserine, terizidone, ansamycin, lysostaphin, iclaprim, mirocin B17, clerocidin, filgrastim and pentamidine;
- antiviral agents, including aziclovir, ganciclovir, brivudin, valaciclovir, zidovudine, didanosine, thiacytidine, stavudine, lamivudine, zalcitabine, ribavirine, nevirapirine, delaviridine, trifluridine, ritonavir, saquinavir, indinavir, foscarnet, amantadine, podophyllotoxin, vidarabine, tromantadine and proteinase inhibitors;
- antiseptics, including acridine derivatives, iodine providon, benzoates, rivanol, chlorhexidine, quaternary ammonium compounds, cetrimides, biphenylol, chlorophen and octenidine;
- plant extracts or components, such as plant extracts of camomile, hamamelis, Echinacea, calendula, thyme, papain, pelargonium, pine trees, essential oils, myrtol, pinene, limonene, cineole, thymol, menthol, camphor, tannin, alpha-hederin, bisabolol, lycopodine, vitapherol;
- wound-treating compounds, including dexpanthenol, allantoin, vitamins, hyaluronic acid, alpha-antitrypsin, inorganic and organic zinc salts/compounds, bismuth salts and selenium salts;
- interferons (alpha, beta, gamma), tumour necrosis factors, cytokines, interleukins,
- immunomodulators, including methotrexate, azathioprine, cyclosporine, tacrolismus, sirolismus, rapamycin, mofetil, mofetil-mycophenolate;
- cytostatic agents and metastase inhibitors;
- alkylating agents, such as nimustin, melphalan, carmustine, lomustine, cyclophosphamide, ifosfamide, trofosfamide, chloroambucil, busulfan, treosulfan, prednimustine, thiotepa;
- anti-metabolites, for example cytarabine, fluorouracil, methotrexate, mercaptopurine, thioguanine;
- alkaloids such as vinblastine, vincristine, vindesine;
- antibiotics such as, for example, alcarubicin, bleomycin, dactinomycin, daunorubicin, doxorubicin, epirubicin, idarubicin, mitomycin, plicamycin;
- complexes of transitional elements (for example, Ti, Zr, V, Nb, Ta, Mo, W, Pt) such as carboplatinim, cis-platinum and metallocene compounds such as, for example, titanocene dichloride;
- amsacrine, dacarbazine, estramustine, etoposide, beraprost, hydroxycarbamide, mitoxanthrone, procarbazine, temiposide;
- paclitaxel, iressa, zactima, poly-ADP-ribose-polymerase (PRAP) enzyme inhibitors, banoxantrone, gemcitabine, pemetrexed, bevacizumab, ranibizumab.

Examples of potentially useful mucolytic agents are DNase, P2Y2-agonists (denufosol), medicaments that affect the penetration of chlorine and sodium, such as, for example, N-(3,5-diamino-6-chloropyrazine-2-carbonyl)-N'-{4-[4-(2,3-dihydroxypropoxy)-phenyl]butyl}guanidine-methane sulfonate (PARION 552-02) heparinoids, guaifenesine, acetylcysteine, carbocysteine, ambroxol, bromhexine, tyloxapol, lecithine, myrtol and recombinant surfactant proteins.

Examples of potentially useful vasoconstrictors and decongestants that may be useful for reducing swelling of the mucous membrane are phenylephrine, naphazoline, tramazoline, tetryzoline, oxymetazoline, fenoxazoline, xylometazoline, epinephrine, isoprenaline, hexoprenaline and ephedrine.

Examples of potentially useful local anaesthetics include benzocaine, tetracaine, procaine, lidocaine and bupivacaine.

Examples of potentially useful anti-allergy agents include the aforementioned glucocorticoids, cromolyn sodium, nedocromil, cetrizine, loratidine, montelukast, roflumilast, ziluton, omalizumab, heparinoids and other antihistamines, including azelastine, cetirizine, desloratadine, ebastine, fexofenadine, levocetirizine, loratadine.

Antisense oligonucleotides are short synthetic strands of DNA (or analogues) which are complementary or opposite to the target sequence (DNA, RNA) and which are designed such that they stop a biological process such as transcription, translation or splicing. The inhibition of gene expression hereby caused makes oligonucleotides useful for the treatment of many illnesses, depending on their composition, and numerous compounds are currently being clinically tested, such as, for example, ALN-RSV01 for the treatment of respiratory syncytial virus, AVE-7279 for the treatment of asthma and allergies, TPI-ASM8 for the treatment of allergic asthma and 1018-ISS for the treatment of cancer.

Examples of potentially useful peptides and proteins include amino acids, such as, for example, L-arginine, L-lysine, antibodies to toxins produced from microorganisms, antimicrobial peptides such as cecropins, defensins, thionins and cathelicidins.

For each of these and other explicitly mentioned examples of medicament substances that are potentially useful for carrying out the invention, the compound names specified herein should be understood as also including any pharmaceutically acceptable salts, solvates or other hydrates, prodrugs, isomers or any other chemical or physical forms of the relevant compounds which contain the corresponding active residues.

The invention claimed is:

1. A disposable ampoule for use in an aerosol generating device, comprising:

a medicament container that contains a medicament and is formed of a container body and a container bottom extending in a plane perpendicular to a longitudinal direction of the ampoule, a predetermined break point that at least partly surrounds the container bottom, and a fixing groove formed in the container body, the fixing groove being provided centrally or closer to the container bottom in the longitudinal direction of the ampoule to absorb forces required to open the ampoule in the aerosol generating device and which arise when breaking the predetermined break point, wherein the ampoule at least at its inner contour tapers inwardly toward the container bottom in a first functional area of the container body and containing the container bottom, and a second functional area of the container body is substantially configured as a hollow cylinder, wherein the fixing groove includes an annular indentation into the container body and first and second portions of the container body located on opposite sides of the annular indentation, the first and second portions being raised with respect to a bottom part of the annular indentation and defining the annular indentation between them wherein the fixing groove is located between the first functional area and the second functional area, wherein at least one reinforcing rib is provided on the container body and wherein the reinforcing rib extends over a partial area of the container body, over and beyond the container bottom and over at least a partial area of a collar that surrounds the predetermined break point at its outside and extends the container body over and beyond the container bottom, an open end of the collar being spaced from the container body.

2. The ampoule according to claim 1, wherein the fixing groove extends in an annular manner around the container body.

3. The ampoule according to claim 1, wherein the reinforcing rib is provided on a side of the container bottom relative to the fixing groove.

4. The ampoule according to claim 1, wherein two diametrically opposed reinforcing ribs are provided.

5. The ampoule according to claim 1, wherein starting from the container bottom, the collar expands in a conical manner at least at its inner contour.

6. The ampoule according to claim 1, wherein the fixing groove is configured to mount the ampoule in the aerosol generating device and to retain the ampoule in a longitudinal direction of the ampoule.

7. The ampoule according to claim 6, wherein the fixing groove is configured to engage with catches of a translationally moveable element of the aerosol generating device.

8. The ampoule according to claim 7, wherein the fixing groove retains the ampoule in the translationally moveable element of the aerosol generating device, whereby the container bottom is pierced by a translational movement of the translationally moveable element and the retained ampoule relative to a hollow piercing element to open the ampoule and supply the medicament to the aerosol generating device.

9. The ampoule according to claim 1, wherein all parts of the ampoule are integrally formed.

10. The ampoule according to claim 9, which is produced by a blow-fill-seal process.

11. The ampoule according to claim 9, which is made of polyethylene, polypropylene or a thermoplastic copolymer.

12. The ampoule according to claim 1, wherein the medicament contains at least one active agent.

13. The ampoule according to claim 12, wherein the medicament contains at least one auxiliary agent in dissolved or suspended form.

14. The use of an ampoule according to claim 1 in an aerosol generating device, the medicament thereof being nebulized by an aerosol generator and being used for a local, nasal or pulmonary application.

15. The ampoule according to claim 1, wherein the predetermined break point at least partly surrounds the container bottom in the plane of the container bottom.

* * * * *